(12) United States Patent
Xu et al.

(10) Patent No.: US 11,253,221 B2
(45) Date of Patent: Feb. 22, 2022

(54) SYSTEMS AND METHODS FOR CONFIGURING MEDICAL DEVICE

(71) Applicant: SHANGHAI UNITED IMAGING HEALTHCARE CO., LTD., Shanghai (CN)

(72) Inventors: Yiwen Xu, Shanghai (CN); Yangyang Lin, Shanghai (CN); Jiawen Zhou, Shanghai (CN); Jie Yu, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 1101 days.

(21) Appl. No.: 15/846,166

(22) Filed: Dec. 18, 2017

(65) Prior Publication Data

US 2018/0344281 A1 Dec. 6, 2018

(30) Foreign Application Priority Data

Jun. 1, 2017 (CN) .......................... 201710405567.0
Sep. 27, 2017 (CN) .......................... 201710891315.3

(51) Int. Cl.
*A61B 6/00* (2006.01)
*G01R 33/30* (2006.01)
(Continued)

(52) U.S. Cl.
CPC ............. *A61B 6/545* (2013.01); *A61B 6/548* (2013.01); *A61B 6/58* (2013.01); *G01R 33/30* (2013.01);
(Continued)

(58) Field of Classification Search
CPC .......... A61B 6/545; A61B 6/58; A61B 6/548; A61B 6/5294; A61B 6/4435; A61B 6/582;
(Continued)

(56) References Cited

U.S. PATENT DOCUMENTS 7,623,622 B2 * 11/2009 Camus ................. A61B 6/4441
378/108
2005/0020898 A1 1/2005 Vosniak et al.
(Continued)

FOREIGN PATENT DOCUMENTS

CN 1856290 A 11/2006
CN 101217649 A 7/2008
(Continued)

OTHER PUBLICATIONS

First Office Action in Chinese Application No. 201710405567.0 dated Mar. 29, 2019, 22 pages.
(Continued)

*Primary Examiner* — Sean D Mattson
(74) *Attorney, Agent, or Firm* — Metis IP LLC

(57) ABSTRACT

The present disclosure relates to systems and methods for configuring a medical device for a medical procedure. The systems may perform the methods to initialize a gantry angle of a medical device of a new scan. The systems may also perform the methods to obtain a pre-set gantry angle associated with the new scan. The systems may also perform the methods to determine whether the initialized gantry angle is consistent with the pre-set gantry angle. The systems may also perform the methods to adjust the initialized gantry angle of the medical device to the pre-set gantry angle in response to a determination that the initialized gantry angle is inconsistent with the pre-set gantry angle.

18 Claims, 8 Drawing Sheets

(51) Int. Cl.
*G16H 40/67* (2018.01)
*G16H 40/63* (2018.01)
*G01R 33/54* (2006.01)
*G16H 10/60* (2018.01)
*A61B 5/11* (2006.01)

(52) U.S. Cl.
CPC .............. *G16H 40/63* (2018.01); *G16H 40/67* (2018.01); *A61B 5/1113* (2013.01); *A61B 6/4435* (2013.01); *A61B 6/547* (2013.01); *G01R 33/543* (2013.01); *G16H 10/60* (2018.01)

(58) Field of Classification Search
CPC ......... A61B 6/547; A61B 6/563; A61B 8/565; A61B 8/54; A61B 8/585; G01R 33/30; G01R 33/543; A61N 1/38
See application file for complete search history.

(56) References Cited

U.S. PATENT DOCUMENTS

| | | | |
|---|---|---|---|
| 2005/0267348 A1* | 12/2005 | Wollenweber | A61B 6/544 600/407 |
| 2006/0072700 A1 | 4/2006 | Chen et al. | |
| 2007/0053503 A1* | 3/2007 | Zelnik | A61B 6/04 378/205 |
| 2009/0116616 A1 | 5/2009 | Lu et al. | |
| 2011/0069810 A1* | 3/2011 | Kondo | A61B 6/0487 378/15 |
| 2012/0116374 A1 | 5/2012 | Jia et al. | |
| 2014/0193053 A1 | 7/2014 | Kadoury et al. | |
| 2015/0085971 A1 | 3/2015 | Braun et al. | |
| 2020/0000421 A1 | 1/2020 | Xu | |

FOREIGN PATENT DOCUMENTS

| | | | |
|---|---|---|---|
| CN | 101254111 A | | 9/2008 |
| CN | 101496726 A | | 8/2009 |
| CN | 101596112 A | | 12/2009 |
| CN | 201664310 U | | 12/2010 |
| CN | 202154694 U | | 3/2012 |
| CN | 102902889 A | | 1/2013 |
| CN | 203314986 U | | 12/2013 |
| CN | 105232077 A | | 1/2016 |
| CN | 105455634 A | | 4/2016 |
| CN | 105455834 A | * | 4/2016 |
| CN | 105496431 A | | 4/2016 |
| CN | 106852697 A | | 6/2017 |
| CN | 106859676 A | | 6/2017 |
| GB | 1558710 A | | 1/1980 |
| JP | 2002186608 A | | 7/2002 |
| JP | 2004208952 A | | 7/2004 |

OTHER PUBLICATIONS

First Office Action in Chinese Application No. 201710891315.3 dated Mar. 18, 2020, 14 pages.
The Third Office Action in Chinese Application No. 201710405567.0 dated May 27, 2020, 26 pages.

* cited by examiner

SYSTEMS AND METHODS FOR CONFIGURING MEDICAL DEVICE

CROSS-REFERENCE TO RELATED APPLICATIONS

This application claims priority to Chinese Application No. 201710405567.0 filed on Jun. 1, 2017, and Chinese Application No. 201710891315.3 filed on Sep. 27, 2017, the contents of which are incorporated herein by reference in their entirety.

TECHNICAL FIELD

The present disclosure generally relates to systems and methods for operating a medical device for a medical procedure, and more particularly, to systems and methods for configuring a medical device before performing a medical procedure on a target object.

BACKGROUND

Modern medical science increasingly relies on medical devices. Examination methods based on medical devices include X-ray imaging, computed tomography (CT) imaging, magnetic resonance imaging (MRI), ultrasound, endoscope, angiography, etc. Before a medical device starts to scan a patient, the medical device may be configured to be in a work mode that complies with the medical procedure to be performed on the patient. The configuration usually takes a long time. In general, the configuration of the medical device may be performed after the patient is ready for the scan (e.g., the patient has lain on a scanning table of the medical device for scanning), which is time inefficient and makes the patient uncomfortable. Therefore, it is desirable to provide systems and methods for configuring a medical device to improve the efficiency of a scan procedure.

SUMMARY

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

According to an aspect of the present disclosure, a system for configuring a medical device for a medical procedure may include one or more storage media and one or more processors configured to communicate with the one or more storage media. The one or more storage media may include a set of instructions. When the one or more processors executing the set of instructions, the one or more processors may be directed to perform one or more of the following operations. The one or more processors may initialize a gantry angle of a medical device of a new scan. The one or more processors may obtain a pre-set gantry angle associated with the new scan. The one or more processors may determine whether the initialized gantry angle is consistent with the pre-set gantry angle. The one or more processors may adjust the initialized gantry angle of the medical device to the pre-set gantry angle in response to a determination that the initialized gantry angle is inconsistent with the pre-set gantry angle.

In some embodiments, to initialize the gantry angle of the medical device, the one or more processors may acquire one or more prior gantry angle values of the medical device, the one or more prior gantry angle values corresponding to one or more prior scans performed prior to a current time. The one or more processors may initialize the gantry angle of the medical device based on the one or more prior gantry angle values.

In some embodiments, to initialize the gantry angle of the medical device based on the one or more prior gantry angle values, the one or more processors may determine an average value of the one or more prior gantry angle values. The one or more processors may initialize the gantry angle of the medical device to the average value of the one or more prior gantry angle values.

In some embodiments, to initialize the gantry angle of the medical device based on the one or more prior gantry angle values, the one or more processors may divide the one or more prior gantry angle values into one or more groups each of which includes one or more equal prior gantry angle values. For each of the one or more groups, the one or more processors may determine a number of equal prior gantry angle values of the group. The one or more processors may select, from the one or more groups, at least one group of which the number of equal prior gantry angle values is maximum among the one or more groups.

In some embodiments, to initialize the gantry angle of the medical device based on the one or more prior gantry angle values, the one or more processors may determine that a number of the selected at least one group is one. The one or more processors may initialize the gantry angle of the medical device to the prior gantry angle value corresponding to the selected group in response to the determination.

In some embodiments, to initialize the gantry angle of the medical device based on the one or more prior gantry angle values, the one or more processors may determine that a number of the selected at least one group is more than one. The one or more processors may obtain a prior time instant corresponding to each of the prior gantry angle values in the selected at least one group in response to the determination. The one or more processors may determine one of the prior gantry angle values in the selected at least one group with the prior time instant closest to the current time. The one or more processors may initialize the gantry angle of the medical device to the one of the prior gantry angle values in the selected at least one group with the prior time instant closest to the current time.

In some embodiments, to initialize the gantry angle of the medical device based on the one or more prior gantry angle values, the one or more processors may determine that a number of the selected at least one group is more than one. The one or more processors may determine an average value of the prior gantry angle values corresponding to the selected at least one group in response to the determination. The one or more processors may initialize the gantry angle of the medical device to the average value of the prior gantry angle values corresponding to the selected at least one group.

In some embodiments, before initializing the gantry angle of the medical device of the new scan, the one or more processors may determine that a prior scan performed closest to a current time has been completed by the medical device.

According to another aspect of the present disclosure, a method for configuring a medical device for a medical procedure may include one or more of the following operations. One or more processors may initialize a gantry angle of a medical device of a new scan. The one or more processors may obtain a pre-set gantry angle associated with the new scan. The one or more processors may determine whether the initialized gantry angle is consistent with the pre-set gantry angle. The one or more processors may adjust the initialized gantry angle of the medical device to the pre-set gantry angle in response to a determination that the initialized gantry angle is inconsistent with the pre-set gantry angle.

According to yet another aspect of the present disclosure, a non-transitory computer readable medium may comprise executable instructions. When executed by one or more processors, the executable instructions may cause the one or more processors to effectuate one or more of the following operations. The one or more processors may initialize a gantry angle of a medical device of a new scan. The one or more processors may obtain a pre-set gantry angle associated with the new scan. The one or more processors may determine whether the initialized gantry angle is consistent with the pre-set gantry angle. The one or more processors may adjust the initialized gantry angle of the medical device to the pre-set gantry angle in response to a determination that the initialized gantry angle is inconsistent with the pre-set gantry angle.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "module," and/or "block" used herein are one method to distinguish different components, elements, parts, section or assembly of different level in ascending order. However, the terms may be displaced by other expression if they achieve the same purpose.

Figure 2:
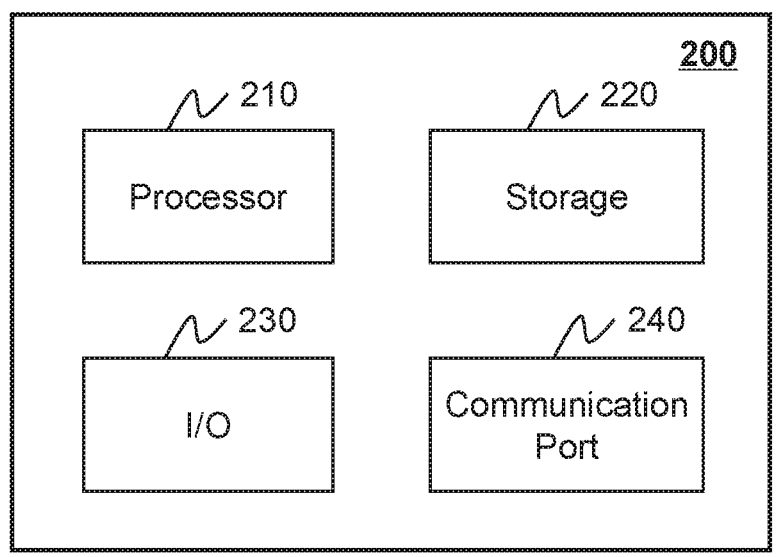
FIG. 2 is a schematic diagram illustrating exemplary hardware and/or software components of a computing device according to some embodiments of the present disclosure.

Generally, the word "module," or "block," as used herein, refers to logic embodied in hardware or firmware, or to a collection of software instructions. A module, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., the processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an Electrically Programmable Read-Only-Memory (EPROM). It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a module or block is referred to as being "connected to," or "coupled to," another module, or block, it may be directly connected or coupled to, or communicate with the other module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

An aspect of the present disclosure relates to systems and methods for configuring a medical device before a scan is performed on a patient. A processing device (e.g., a console) may determine the environment of a scanning room in real time, for example, whether a patient has entered the scanning room, and start to adjust the medical device from a standby mode to a work mode when it is determined that a patient has entered the scanning room. Alternatively or additionally, the processing device may initialize a gantry angle of the medical device, and then adjust the initialized gantry angle to a pre-set gantry angle that is used in a scan to be performed on a target object.

Figure 1:
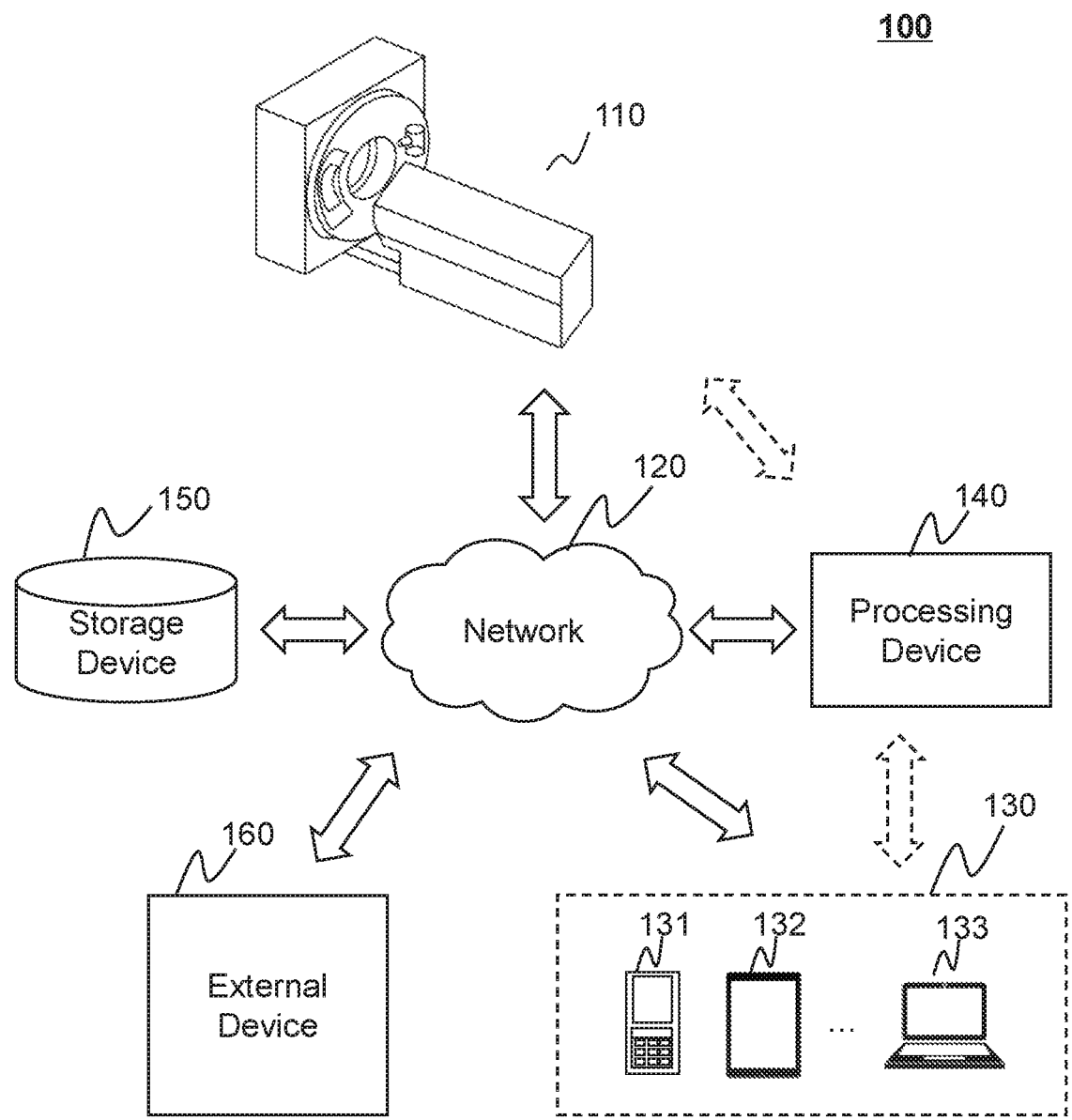
FIG. 1 is a schematic diagram illustrating an exemplary adjustment system according to some embodiments of the present disclosure.

FIG. 1 is a schematic diagram illustrating an exemplary adjustment system 100 according to some embodiments of the present disclosure. As shown in FIG. 1, the adjustment system 100 may include a medical device 110, a network 120, a terminal 130, a processing device 140, a storage device 150, and an external device 160. The components of the adjustment system 100 may be connected in one or more of various ways. Mere by way of example, as illustrated in FIG. 1, the medical device 110 may be connected to the processing device 140 through the network 120. As another example, the medical device 110 may be connected to the processing device 140 directly (as indicated by the bi-directional arrow in dotted lines linking the medical device 110 and the processing device 140). As a further example, the storage device 150 may be connected to the processing device 140 directly or through the network 120. As still a further example, a terminal device (e.g., 130-1, 130-2, 130-3, etc.) may be connected to the processing device 140 directly (as indicated by the bi-directional arrow in dotted lines linking the terminal 130 and the processing device 140) or through the network 120.

The medical device 110 may scan an object (also referred to as a target object). The object may be biological or non-biological. Merely by way of example, the object may include a patient, a man-made object, etc. As another example, the object may include a specific portion, organ, and/or tissue of the patient. For example, the object may include head, brain, neck, body, shoulder, arm, thorax, cardiac, stomach, blood vessel, soft tissue, knee, feet, or the like, or any combination thereof.

The medical device 110 may include a computed radiography (CR) scanner, a digital radiography (DR) scanner, a digital subtraction angiography (DSA) scanner, a computed tomography (CT) scanner, an electroconvulsive therapy (ECT) scanner, a magnetic resonance imaging (MRI) scanner, an ultrasonography scanner, an X-ray photography scanner, a positron emission computed tomography (PET) scanner, a multimodality scanner, or the like, or any combination thereof. Exemplary multi-modality scanner may include a CT-PET scanner, a CT-MRI scanner, a PET-MRI scanner, etc.

The network 120 may include any suitable network that can facilitate exchange of information and/or data for the adjustment system 100. In some embodiments, one or more components of the adjustment system 100 (e.g., the medical device 110, the terminal 130, the processing device 140, the storage device 150, etc.) may communicate information and/or data with one or more other components of the adjustment system 100 via the network 120. For example, the processing device 140 may obtain information relating to an object (e.g., a patient) from the storage device 150 via the network 120. As another example, the processing device 140 may obtain user instructions from the terminal 130 via the network 120. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, witches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the adjustment system 100 may be connected to the network 120 to exchange data and/or information.

The terminal 130 may include a mobile device 130-1, a tablet computer 130-2, a laptop computer 130-3, or the like, or any combination thereof. In some embodiments, the mobile device 130-1 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistance (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing device 140.

The processing device 140 may process data and/or information obtained from the medical device 110, the terminal 130, and/or the storage device 150. For example, the processing device 140 may determine at least one parameter associated with a medical procedure to be performed on the target object based on information relating to the target object. As another example, the processing device 140 may adjust a gantry angle of the medical device 110 before performing a medical procedure on the target object. In some embodiments, the processing device 140 may be a single server or a server group. The server group may be centralized or distributed. In some embodiments, the processing device 140 may be local or remote. For example, the processing device 140 may access information and/or data stored in the medical device 110, the terminal 130, and/or the storage device 150 via the network 120. As another example, the processing device 140 may be directly connected to the medical device 110, the terminal 130 and/or the storage device 150. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2.

The storage device 150 may store data, instructions, and/or any other information. In some embodiments, the storage device 150 may store data obtained from the terminal 130 and/or the processing device 140. In some embodiments, the storage device 150 may store data and/or instructions that the processing device 140 may execute or use to perform exemplary methods described in the present disclosure. In some embodiments, the storage device 150 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components in the adjustment system 100 (e.g., the processing device 140, the terminal 130, etc.). One or more components in the adjustment system 100 may access the data or instructions stored in the storage device 150 via the network 120. In some embodiments, the storage device 150 may be directly connected to or communicate with one or more other components in the adjustment system 100 (e.g., the processing device 140, the terminal 130, etc.). In some embodiments, the storage device 150 may be part of the processing device 140.

The external device 160 may acquire information relating to a target object. The information relating to the target object may include environment information, personal information, registration information, medical record information, a scan protocol, or the like, or a combination thereof of the patient. The environment information may indicate whether there is a person in a certain region (e.g., a scanning room, a registration office, a space above a scanning table of the medical device 110). The personal information of a target object may include the name, the age, the gender, the home address, the phone number, the occupation, the work unit, the date of birth, or the like, or any combination thereof. The registration information of a target object may include an item related to the medical device 110 (e.g., a CT scan of brain, an MRI scan of chest), the payment amount associated with the item, the payment method (e.g., cash payment, mobile payment, bank transfer, credit card payment, debit card payment) associated with the item, an appointment time for the item, or the like, or any combination thereof. The medical record may be a systematic documentation of a patient's medical history and include drugs and therapies for the patient. The processing device may acquire the information relating to the target object from the external device 160. In some embodiments, the external device 160 may include a sensor, a remote information device, or the like, or any combination thereof. The sensor may include an infrared sensor, a pressure sensor, a microwave sensor, a temperature sensor, a light sensitive sensor, a heat sensitive sensor, an image sensor (e.g., a camera), or the like, or a combination thereof. The remote information device may include an electronic system, such as a Hospital Information System (HIS), a Radiology Information System (RIS), a Laboratory Information System (LIS), an Electronic Medical Record (EMR), a Picture Archiving and Communication System (PACS), or the like, or a combination thereof. The HIS may include a finance management system, a personnel management system, a hospital management system, an outpatient management system, a drug management system, or the like, or a combination thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the external device 160 may be omitted.

FIG. 2 is a schematic diagram illustrating exemplary hardware and/or software components of a computing device on which the processing device 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (e.g., program code) and perform functions of the processing device 140 in accordance with techniques described herein. The computer instructions may include, for example, routines, programs, objects, components, data structures, procedures, modules, and functions, which perform particular functions described herein. For example, the processor 210 may determine at least one parameter associated with a medical procedure to be performed on a target object based on information relating to the target object. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both step A and step B, it should be understood that step A and step B may also be performed by two or more different processors jointly or separately in the computing device 200 (e.g., a first processor executes step A and a second processor executes step B, or the first and second processors jointly execute steps A and B).

The storage 220 may store data/information obtained from the medical device 110, the terminal 130, the storage device 150, and/or any other component of the adjustment system 100. In some embodiments, the storage 220 may include a mass storage, a removable storage, a volatile read-and-write memory, a read-only memory (ROM), or the like, or any combination thereof. For example, the mass storage may include a magnetic disk, an optical disk, a solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 140 for adjusting the medical device 110.

The I/O 230 may input and/or output signals, data, information, etc. In some embodiments, the I/O 230 may enable a user interaction with the processing device 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing device 140 and the medical device 110, the terminal 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with digital imaging and communications in medicine (DICOM) protocol.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 3:
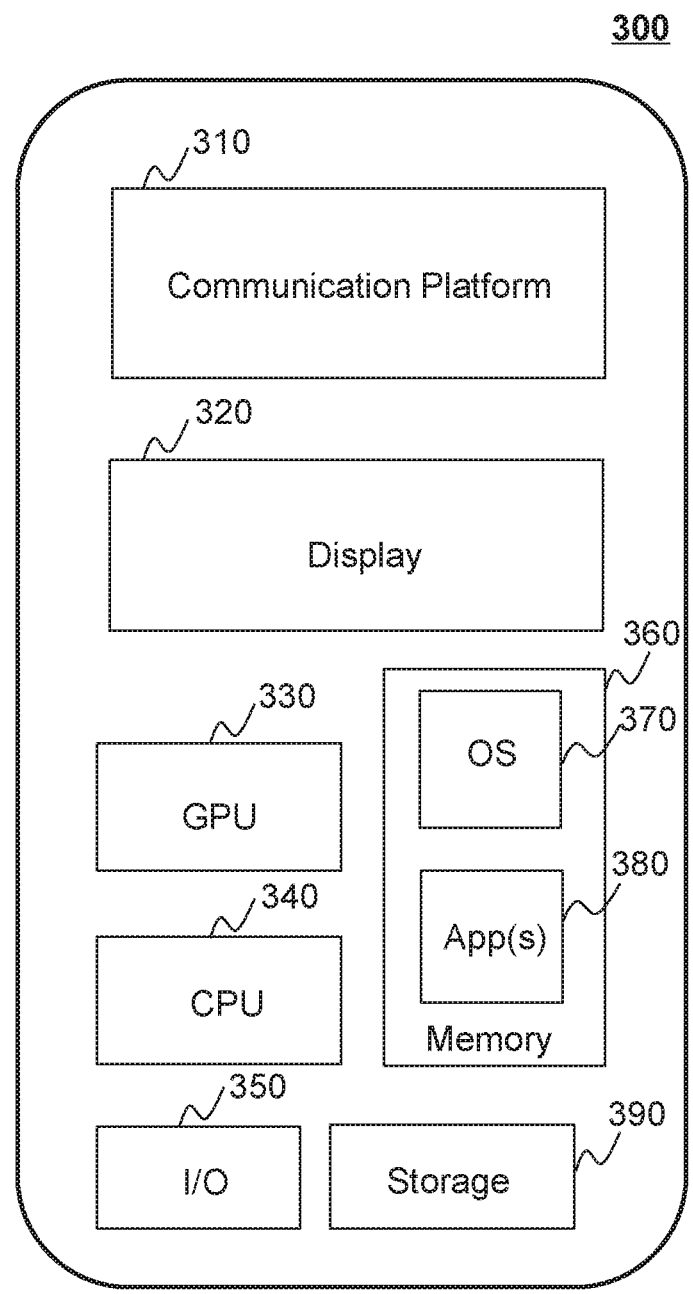
FIG. 3 is a schematic diagram illustrating exemplary hardware and/or software components of a mobile device according to some embodiments of the present disclosure.

FIG. 3 is a schematic diagram illustrating exemplary hardware and/or software components of an exemplary mobile device 300 on which the terminal 130 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the adjustment system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 4:
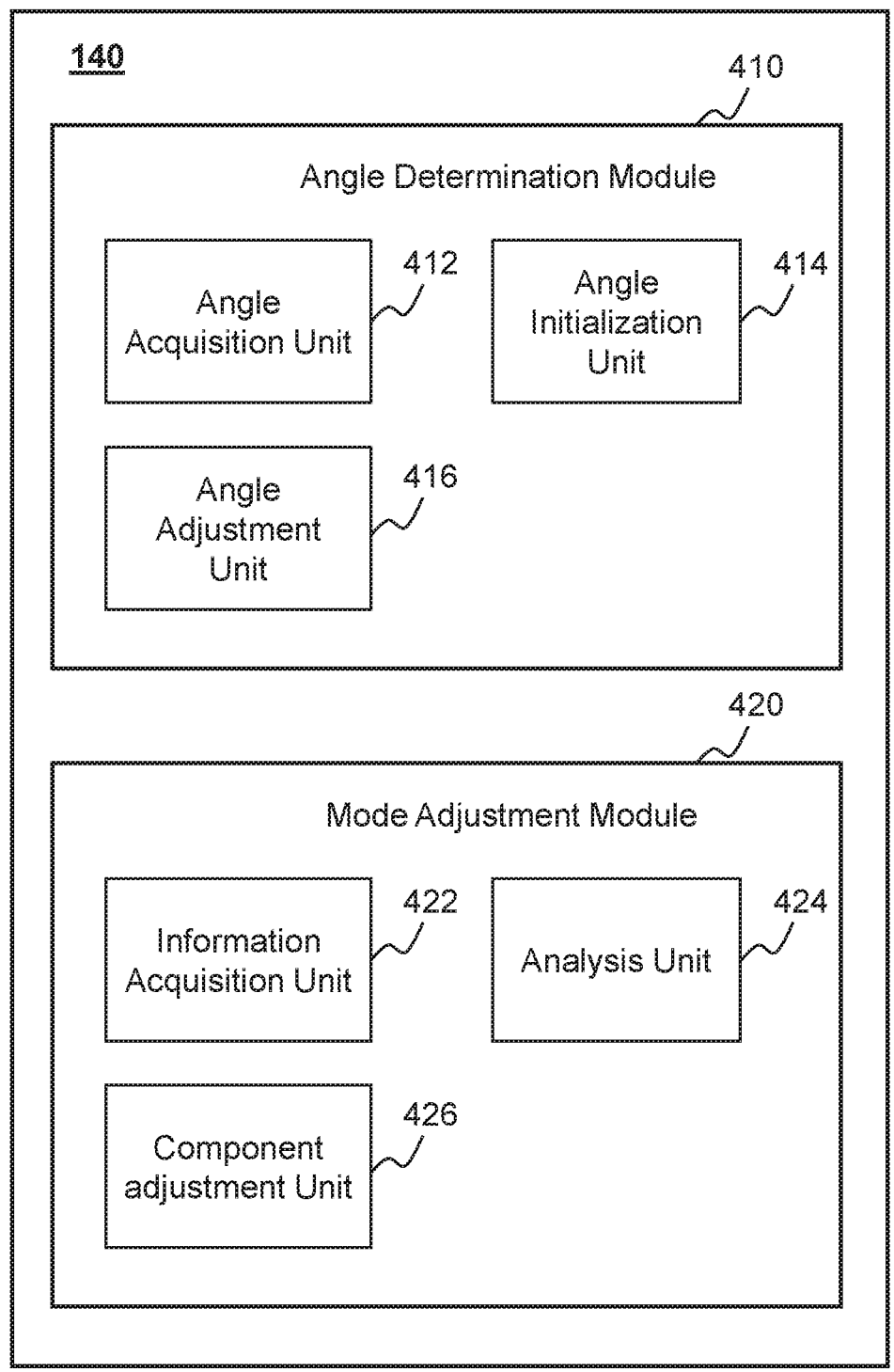
FIG. 4 is a block diagram illustrating an exemplary processing device according to some embodiments of the present disclosure.

FIG. 4 is a block diagram illustrating an exemplary processing device according to some embodiments of the present disclosure. The processing device 140 may include an angle determination module 410 and/or a mode adjustment module 420.

The angle determination module 410 may be configured to initialize a gantry angle of the medical device 110 and adjust the initialized gantry angle to a pre-set gantry angle that is used in a scan to be performed on a target object. The angle determination module 410 may include an angle acquisition unit 412, an angle initialization unit 414, and an angle adjustment unit 416.

The angle acquisition unit 412 may be configured to acquire one or more prior gantry angle values of a medical device (e.g., the medical device 110). For example, for a CT scanner, an X-ray source of the CT scanner may rotate together with a gantry of the CT scanner. A gantry angle value may indicate a location of the X-ray source. For example, if the X-ray source is rotated to a location corresponding to 3 o'clock, the gantry angle value is 90°. As another example, if the X-ray source is rotated to a location corresponding to 9 o'clock, the gantry angle value is 270°.

In some embodiments, a prior gantry angle value may refer to a gantry angle value that was used in a previous scan prior to the current time. For example, the angle determination module 410 may acquire prior gantry angle values used in the past 30 days. In some embodiments, the one or more prior gantry angle values may correspond to a same medical device.

The angle initialization unit 414 may be configured to initialize a gantry angle of the medical device (e.g., the medical device 110) to Degree 0 (e.g., a gantry angle) based on the one or more prior gantry angle values. In some embodiments, Degree 0 was mostly frequently used during a certain period (e.g., past 30 days from the current time) among the one or more prior gantry angle values. In some embodiments, initializing the gantry angle of the medical device using Degree 0 may reduce the time of adjusting the X-ray source to a gantry angle for a scan to be performed on the target object. Description regarding the determination of a gantry angle value of Degree 0 may be found elsewhere in the present disclosure. See, e.g., FIG. 7, and the description thereof.

The angle adjustment unit 416 may be configured to acquire a pre-set gantry angle Degree 1. In some embodiments, the pre-set gantry angle may be used to a scan to be performed on the target object. The angle determination module 410 may acquire the pre-set gantry angle based on a scan protocol.

The angle adjustment unit 416 may also be configured to determine whether Degree 0 is equal to Degree 1. The angle adjustment unit 416 may adjust the gantry angle from Degree 0 to Degree 1 in response to a determination that Degree 0 is not equal to Degree 1. The angle adjustment unit 416 may keep the gantry angle at Degree 0 in response to a determination that Degree 0 is equal to Degree 1.

The mode adjustment module 420 may be configured to adjust the medical device 110 from a standby mode to a work mode. The mode adjustment module 420 may include an information acquisition unit 422, an analysis unit 424, and a component adjustment unit 426.

The information acquisition unit 422 may be configured to acquire information relating to a target object. The information relating to the target object may include environment information, personal information, registration information, medical record information, a scan protocol, or the like, or a combination thereof of the patient. The environment information may indicate whether there is a person in a certain region (e.g., a scanning room, a registration office, a space above a scanning table of the medical device 110). The personal information of a target object may include the name, the age, the gender, the home address, the phone number, the occupation, the work unit, the date of birth, or the like, or any combination thereof. The registration information of a target object may include an item related to the medical device 110 (e.g., a CT scan of brain, an MRI scan of chest), the payment amount associated with the item, the payment method (e.g., cash payment, mobile payment, bank transfer, credit card payment, debit card payment) associated with the item, an appointment time for the item, or the like, or any combination thereof. The medical record may be a systematic documentation of a patient's medical history and include drugs and therapies for the patient.

The scan protocol may be designed with respect to one or more tissues to be imaged, diseases to be diagnosed, and/or clinical scenarios. The scan protocol may include one or more parameters associated with the scan of the target object. The scan protocols for different medical devices or different target objects may be different. For example, for an MRI scan, the scan protocol may include a certain number of pulse sequences. The pulse sequences may include spin echo sequences, gradient echo sequences, diffusion sequences, inversion recovery sequences, or the like, or any combination thereof. For instance, the spin echo sequences may include fast spin echo (FSE), turbo spin echo (TSE), rapid acquisition with relaxation enhancement (RARE), half-Fourier acquisition single-shot turbo spin-echo (HASTE), turbo gradient spin echo (TGSE), or the like, or any combination thereof. For an MRI scan, the scan protocol may also include image contrast and/or ratio, a region of interest (ROI), slice thickness, an imaging type (e.g., T1 weighted imaging, T2 weighted imaging, proton density weighted imaging, etc.), a spin echo type (spin echo, fast spin echo (FSE), fast recovery FSE, single shot FSE, gradient recalled echo, fast imaging with stead-state procession, and so on), a flip angle value, acquisition time (TA), echo time (TE), repetition time (TR), echo train length (ETL), the number of phases, the number of excitations (NEX), inversion time, bandwidth (e.g., radiofrequency (RF) receiver bandwidth, RF transmitter bandwidth, etc.), or the like, or any combination thereof. As another example, for a CT scan, the scan protocol may include a gantry angle, a radiation dose of X-rays emitted from an X-ray source, a scan period, a gantry location, a rotation speed of the gantry, the number of times the gantry rotates, or the like, or any combination thereof.

In some embodiments, the mode adjustment module 420 may acquire the information relating to the target object through at least one of one or more sensors, one or more remote information devices, one or more human machine interaction devices, and software implemented by the processing device 140.

The analysis unit 424 may be configured to make a determination by analyzing information related to the scan to be performed on a target object. In some embodiments, the analysis unit 424 may determine whether there is a scan to be performed on the target object by analyzing the information relating to the target object. In some embodiments, the analysis unit 424 may determine whether the medical device 110 has completed the scan performed on the target object. In some embodiments, the analysis unit 424 may determine whether the medical device 110 satisfies a condition to get into a standby mode.

The component adjustment unit 426 may be configured to adjust the medical device 110 between the standby mode and the work mode. In some embodiments, the component adjustment unit 426 may adjust the medical device 110 from the standby mode to the work mode to perform the scan on the target object based on the scan protocol in response to a determination that there is a scan to be performed on the target object. In some embodiments, after the medical device 110 has completed the scan performed on the target object, the component adjustment unit 426 may adjust the medical device 110 to the standby mode in response to a determination that the medical device satisfies a condition to get into the standby mode.

The modules and/or units in the processing engine 140 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules (or units) may be combined as a single module (or unit), and any one of the modules (or units) may be divided into two or more units (or blocks). For example, the angle determination module 410 may be integrated in the mode adjustment module 420 as a single module which may adjust the gantry angle and adjust the medical device 110 between a standby mode and a work mode. As another example, the information acquisition unit 422 may include four individual blocks that can be implemented as separate units. The first block may be configured to acquire the information relating to the target object through one or more sensors. The second block may be configured to acquire the information relating to the target object through one or more remote information devices. The third block may be configured to acquire the information relating to the target object through one or more human machine interaction devices. The fourth block may be configured to acquire the information relating to the target object through one or more software implemented by the processing device 140.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 140 may further include a storage module (not shown in FIG. 4). The storage module may be configured to store data generated during any process performed by any component of in the processing device 140. As another example, each of components of the processing device 140 may include a storage apparatus. Additionally or alternatively, the components of the processing device 140 may share a common storage apparatus. As still another example, the angle determination module 410 or the mode adjustment module 420 may be omitted.

Figure 5:
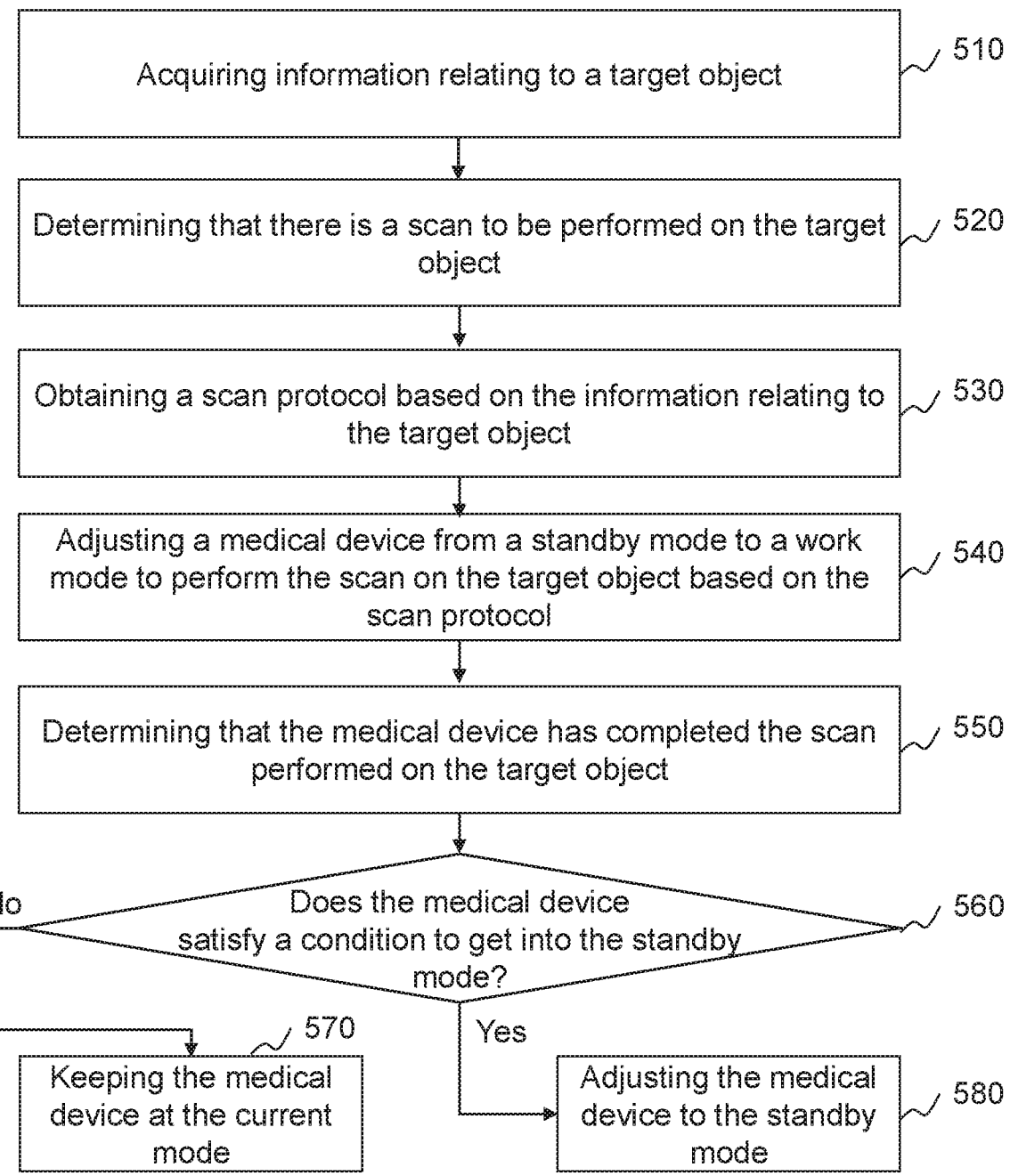
FIG. 5 is a flowchart illustrating an exemplary process for adjusting a medical device to be in a work mode according to some embodiments of the present disclosure.

FIG. 5 is a flowchart illustrating an exemplary process for adjusting a medical device according to some embodiments of the present disclosure. The process 500 may be implemented in the adjustment system 100 illustrated in FIG. 1. For example, the process 500 may be stored in the storage device 150 and/or the storage 220 in the form of instructions (e.g., an application), and invoked and/or executed by the processing device 140 (e.g., the processor 210 illustrated in FIG. 2, or one or more modules in the processing device 140 illustrated in FIG. 4). The operations of the illustrated process presented below are intended to be illustrative. In some embodiments, the process 500 may be accomplished with one or more additional operations not described, and/or without one or more of the operations discussed. Additionally, the order in which the operations of the process 500 as illustrated in FIG. 5 and described below is not intended to be limiting.

In 510, the mode adjustment module 420 (e.g., the information acquisition unit 422) may acquire information relating to a target object. The information relating to the target object may include environment information, personal information, registration information, medical record information, a scan protocol, or the like, or a combination thereof of the patient. The environment information may indicate whether there is a person in a certain region (e.g., a scanning room, a registration office, a space above the scanning table of the medical device 110). The personal information of a target object may include the name, the age, the gender, the home address, the phone number, the occupation, the work unit, the date of birth, or the like, or any combination thereof. The registration information of a target object may include an item related to a medical procedure, the payment amount associated with the item, the payment method (e.g., cash payment, mobile payment, bank transfer, credit card payment, debit card payment) associated with the item, an appointment time for the item, or the like, or any combination thereof. The medical record may be a systematic documentation of a patient's medical history and include drugs and therapies for the patient.

The scan protocol may be designed with respect to one or more tissues to be imaged, diseases to be diagnosed, and/or clinical scenarios. The scan protocol may include one or more parameters associated with the scan of the target object. For example, the scan protocol may include a type of the medical device used in the scan, a region of interest (ROI) of the target object, the duration of the scan, the size of a reconstruction image, the resolution of a reconstruction image, or the like, or any combination thereof. The scan protocols for different medical devices or different target objects may be different. For example, for an MRI scan, the scan protocol may include a certain number of pulse sequences. The pulse sequences may include spin echo sequences, gradient echo sequences, diffusion sequences, inversion recovery sequences, or the like, or any combination thereof. For instance, the spin echo sequences may include fast spin echo (FSE), turbo spin echo (TSE), rapid acquisition with relaxation enhancement (RARE), half-Fourier acquisition single-shot turbo spin-echo (HASTE), turbo gradient spin echo (TGSE), or the like, or any combination thereof. For an MRI scan, the scan protocol may also include image contrast and/or ratio, a region of interest (ROI), slice thickness, an imaging type (e.g., T1 weighted imaging, T2 weighted imaging, proton density weighted imaging, etc.), a spin echo type (spin echo, fast spin echo (FSE), fast recovery FSE, single shot FSE, gradient recalled echo, fast imaging with stead-state procession, and so on), a flip angle value, acquisition time (TA), echo time (TE), repetition time (TR), echo train length (ETL), the number of phases, the number of excitations (NEX), inversion time, bandwidth (e.g., radiofrequency (RF) receiver bandwidth, RF transmitter bandwidth, etc.), or the like, or any combination thereof. As another example, for a CT scan, the scan protocol may include a gantry angle, a rotation speed of a gantry, a radiation dose of X-rays emitted from an X-ray source, one or more slices of the target object to be scanned, or the like, or any combination thereof.

In some embodiments, the mode adjustment module 420 may acquire the information relating to the target object through at least one of one or more sensors, one or more remote information devices, one or more human machine interaction devices, and software implemented by the processing device 140.

In some embodiments, the mode adjustment module 420 may acquire the environment information through one or more sensors. The sensor may include an infrared sensor, a pressure sensor, a microwave sensor, a temperature sensor, a light sensitive sensor, a heat sensitive sensor, an image sensor (e.g., a camera), or the like, or a combination thereof.

In some embodiments, one or more infrared sensors may be mounted somewhere in a hospital, such as a scanning room, a registration office, etc. The infrared sensor may acquire infrared signals and/or infrared images within a certain region (e.g., a scanning room, a registration office) constantly and send the acquired infrared signals and/or infrared images to the mode adjustment module 420 in real time or at intervals (e.g., every 2 minutes).

In some embodiments, one or more pressure sensors may be mounted on a scanning table of the medical device 110. The pressure sensor may acquire pressure signals within a certain region (e.g., the scanning table) by, for example, one or more elastic components in the pressure sensor. For example, when a patient lies on the scanning table, one or more pressure sensors mounted on the scanning table may generate pressure signals based on the deformation of the one or more elastic components, and transmit the pressure signals to the mode adjustment module 420.

In some embodiments, one or more temperature sensors may be mounted somewhere in a hospital, such as a scanning room, a registration office, a scanning table, etc. The temperature sensor may acquire a temperature within a certain region (e.g., a scanning room, a registration office) in real time and send the temperature to the mode adjustment module 420 in real time or at intervals (e.g., every 2 minutes). The temperature sensor may include a contact temperature sensor, a non-contact temperature sensor, or the like, or any combination thereof.

In some embodiments, one or more image sensors (e.g., cameras) may be mounted somewhere in a hospital, such as a scanning room, a registration office, a scanning table, etc. The image sensor may acquire two-dimensional (2D) images or three-dimensional (3D) images within a certain region (e.g., a scanning room, a registration office) in real time and send the acquired images to the mode adjustment module 420 in real time or at intervals (e.g., every 2 minutes).

In some embodiments, the mode adjustment module 420 may acquire the personal information, the registration information, or the medical record information from one or more remote information devices. The remote information device may include an electronic system, such as a Hospital Information System (HIS), a Radiology Information System (RIS), a Laboratory Information System (LIS), an Electronic Medical Record (EMR), a Picture Archiving and Communication System (PACS), or the like, or a combination thereof. The HIS may include a finance management system, a personnel management system, a hospital management system, an outpatient management system, a drug management system, or the like, or a combination thereof.

In some embodiments, the mode adjustment module 420 may acquire the information (e.g., the personal information, the registration information, or the medical record information) relating to the target object from one or more human machine interaction devices. In some embodiments, the processing device 140 and a user (e.g., a patient, a doctor, an imaging engineer) may exchange information through the human machine interaction device. For example, the user may download a medical record of a patient through the human machine interaction device. As another example, the human machine interaction device may display a medical image (e.g., an MRI image) to the user though the human machine interaction device. As still another example, the user may input an instruction to control the medical device 110 through the human machine interaction device. The human machine interaction device may include an I/O device, such as a keyboard, a mouse, a display screen, a touch screen, or the like, or any combination thereof. The human machine interaction device may be implemented in the processing device 140 (e.g., the I/O 230), the terminal 130 (e.g., the I/O 350), or the external device 160 communicated with the processing device 140. In some embodiments, the user may input the scan protocol through the human machine interaction device. The human machine interaction device may acquire the scan protocol based on the user's input. In some embodiments, the human machine interaction device may include a human machine interface (HMI).

In some embodiments, the mode adjustment module 420 may acquire the information (e.g., the personal information, the registration information, or the medical record information) relating to the target object through software (e.g., image configuration software, interface configuration software) installed in the processing device 140 and/or the remote information device. When the user input the information (e.g., the personal information, the registration information, the medical record information, the scan protocol) relating to the target object through the software, the software may send the user' input to the mode adjustment module 420 in real time.

In 520, the mode adjustment module 420 (e.g., the analysis unit 424) may determine whether there is a scan to be performed on the target object by analyzing the information relating to the target object. The process 500 may proceed to 530 in response to a determination that there is a scan to be performed on the target object. The process 500 may proceed to 560 in response to a determination that there is no scan to be performed on the target object.

Merely by way of example, the mode adjustment module 420 may determine whether a patient has entered the scanning room by analyzing infrared signals received from one or more infrared sensors mounted in the scanning room.

Merely by way of example, the mode adjustment module 420 may determine whether a patient has lain on the scanning table by analyzing pressure signals received from one or more pressure sensors mounted on the scanning table. In some embodiments, the pressure sensor may acquire pressure signals based on the deformation of one or more elastic components in the pressure sensor. The larger the deformation is, the stronger the strength of the pressure signals may be. The mode adjustment module 420 may determine that a patient has lain on the scanning table in response to a determination that the strength of the pressure signals received from the one or more pressure sensors mounted on the scanning table is greater than a strength threshold.

Merely by way of example, the mode adjustment module 420 may determine whether a patient has lain on the scanning table or has entered the scanning room by analyzing the temperature received from one or more temperature sensors mounted on the scanning table or in the scanning room. In some embodiments, the more the people there are in a certain region, the higher the temperature related to the certain region may be. The mode adjustment module 420 may determine that there is a patient in a certain region (e.g., the scanning room or the scanning table) in response to a determination that a difference between the current temperature and a prior temperature detected in the past (e.g., 5 minutes before the current time) is greater than a threshold temperature (e.g., 2° C.).

Merely by way of example, the mode adjustment module 420 may determine whether a patient has lain on the scanning table or has entered the scanning room by analyzing images received from one or more image sensors (e.g., cameras) mounted on the scanning table or in the scanning room.

In some embodiments, the mode adjustment module 420 may determine whether there is at least one scan relating to the medical device 110 (e.g., a CT scan, an MRI scan) in the items that have been registered. The mode adjustment module 420 may determine an interval between an appointment time of each scan and the current time in response to a determination that there is at least one scan relating to the medical device 110 in the items that have been registered, and determine whether there is at least one interval that is less than a threshold time (e.g., 30 minutes). The mode adjustment module 420 may determine that there is a scan to be performed on the target object in response to at least one of a determination that there is at least one interval that is less than the threshold time, a determination that a patient has entered the scanning room, and a determination that a patient has lain on the scanning table.

In 530, the mode adjustment module 420 (e.g., the information acquisition unit 422) may obtain a scan protocol based on the information relating to the target object. For example, the mode adjustment module 420 may obtain the scan protocol based on a scan related to the medical device 110 of which the appointment time is closest to the current time.

In some embodiments, the scan protocol relating to the target object may be determined in advance and be stored in a storage medium (e.g., the storage device 150, the storage 220). The mode adjustment module 420 may obtain the scan protocol relating to the target object from the storage medium. In some embodiments, a user may input, through the human machine interaction device, the scan protocol relating to the target object after a determination that there is a scan to be performed on the target object based on the information relating to the target object. The mode adjustment module 420 may obtain the scan protocol from the human machine interaction device based on the input of the user.

In 540, the mode adjustment module 420 (e.g., the component adjustment unit 426) may adjust a medical device (e.g., the medical device 110) from a standby mode to a work mode to perform the scan on the target object based on the scan protocol. In some embodiments, the mode adjustment module 420 may adjust the components of the medical device 110 in the standby mode, adjust reconstruction parameters (e.g., the size of a reconstruction image, the number of the detectors of the medical device 110, the resolution of a reconstruction image), or the like, or any combination thereof. For example, for a CT scanner, the mode adjustment module 420 may correct an X-ray source, correct a detector, correct the position of a scanning table, preheat a high-voltage generator, or adjust a gantry angle. In some embodiments, the standby mode may indicate that the medical device 110 is kept on but is not performing a medical procedure (e.g., a scan procedure to a target object).

In some embodiments, the processing device 140 may communicate with one or more medical devices, such as a CT scanner, an MRI scanner, an X-ray scanner, and a PET scanner, etc. The mode adjustment module 420 may adjust one of the one or more medical devices communicating with the processing device 140 based on the information relating to the target object. For example, if the scan corresponding to the target object relates to a CT scan, the mode adjustment module 420 may adjust a CT scanner communicating with the processing device 140.

In some embodiments, the medical device 110 may perform the scan on the target object in the work mode based on the scan protocol.

In 550, the mode adjustment module 420 (e.g., the analysis unit 424) may determine that the medical device (e.g., the medical device 110) has completed the scan performed on the target object. For example, the mode adjustment module 420 may determine that the medical device 110 has completed the scan performed on the target object in response to a determination that the duration of the scan is longer than a threshold value (e.g., 20 minutes). As another example, the mode adjustment module 420 may determine that the medical device 110 has completed the scan performed on the target object based on a user's input (e.g., pressing a button of completion).

In 560, the mode adjustment module 420 (e.g., the analysis unit 424) may determine whether the medical device (e.g., the medical device 110) satisfies a condition to get into the standby mode. For example, the mode adjustment module 420 may determine that the medical device 110 satisfies a condition to get into the standby mode in response to a determination that the power consumption of the medical device 110 at current time is lower than a threshold power. As another example, the mode adjustment module 420 may determine that the medical device 110 satisfies a condition to get into the standby mode in response to a determination that the medical device 110 does not receive any instruction within a certain time interval (e.g., 10 minutes) from the time when the scan is completed.

The process 500 may proceed to 570 to keep the medical device (e.g., the medical device 110) at the current mode (e.g., the work mode) in response to a determination that the medical device (e.g., the medical device 110) does not satisfy a condition to get into the standby mode. The process 500 may proceed to 580 to adjust the medical device (e.g., the medical device 110) to the standby mode in response to a determination that the medical device (e.g., the medical device 110) satisfies a condition to get into the standby mode.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, before 510, the mode adjustment module 420 may determine that the medical device 110 is in the standby mode.

Figure 6:
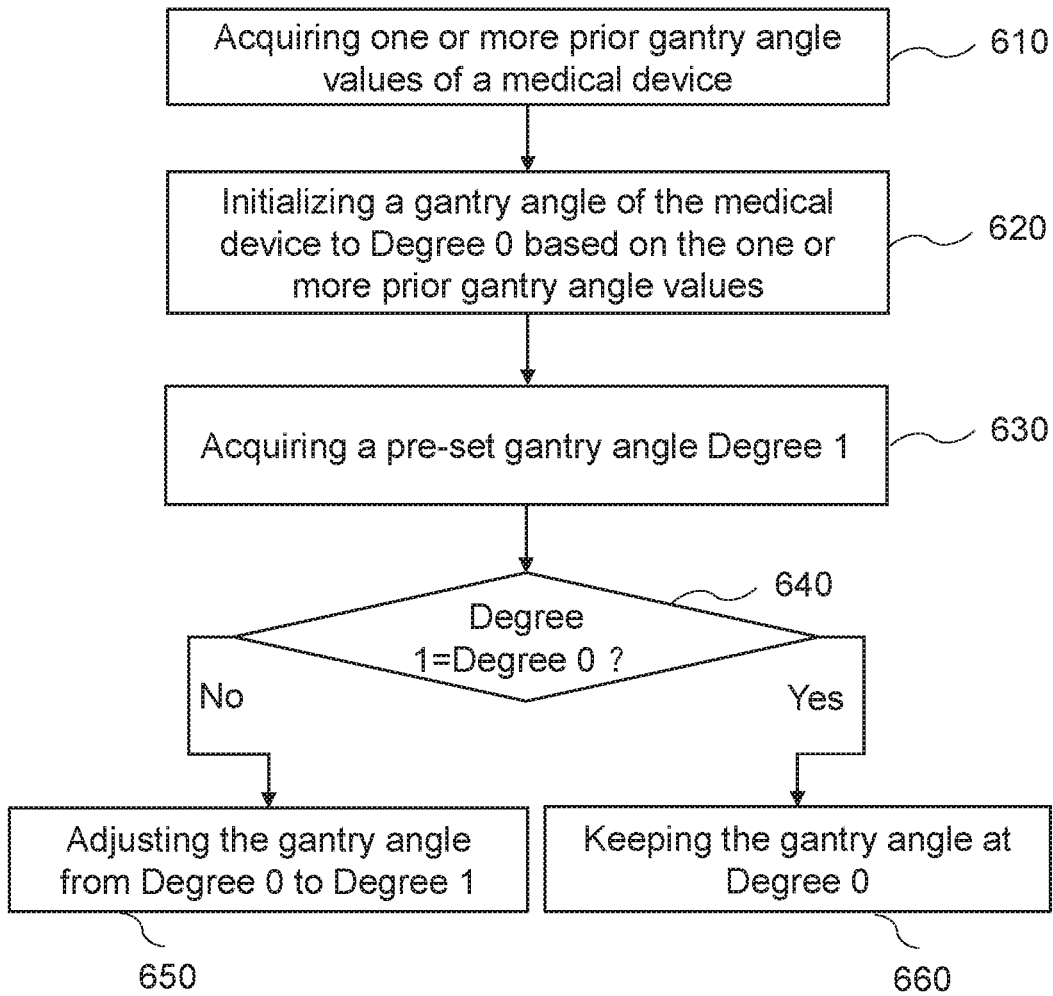
FIG. 6 is a flowchart illustrating an exemplary process for adjusting a gantry angle of a medical device according to some embodiments of the present disclosure.

FIG. 6 is a flowchart illustrating an exemplary process for adjusting a gantry angle of a medical device according to some embodiments of the present disclosure. The process 600 may be implemented in the adjustment system 100 as illustrated in FIG. 1. For example, the process 600 may be stored in the storage device 150 and/or the storage 220 in the form of instructions (e.g., an application), and invoked and/or executed by the processing device 140 (e.g., the processor 210 illustrated in FIG. 2, or one or more modules in the processing device 140 illustrated in FIG. 4). The operations of the illustrated process presented below are intended to be illustrative. In some embodiments, the process 600 may be accomplished with one or more additional operations not described, and/or without one or more of the operations discussed. Additionally, the order in which the operations of the process 600 as illustrated in FIG. 6 and described below is not intended to be limiting.

In 610, the angle determination module 410 (e.g., the angle acquisition unit 412) may acquire one or more prior gantry angle values of a medical device (e.g., the medical device 110). For example, for a CT scanner, an X-ray source of the CT scanner may rotate together with a gantry of the CT scanner. A gantry angle value may indicate a location of the X-ray source. For example, if the X-ray source is rotated to a location corresponding to 3 o'clock, the gantry angle value is 90°. As another example, if the X-ray source is rotated to a location corresponding to 9 o'clock, the gantry angle value is 270°.

In some embodiments, a prior gantry angle value may refer to a gantry angle value that was used in a previous scan prior to the current time. For example, the angle determination module 410 may acquire prior gantry angle values used in the past 30 days. In some embodiments, the one or more prior gantry angle values may correspond to a same medical device.

In 620, the angle determination module 410 (e.g., the angle initialization unit 414) may initialize a gantry angle of the medical device (e.g., the medical device 110) to Degree 0 (e.g., a gantry angle) based on the one or more prior gantry angle values. In some embodiments, the angle determination module 410 may analyze the one or more prior gantry angle values to determine Degree 0 using a moving average forecast algorithm (e.g., a simple moving average algorithm, a double moving average algorithm, a three moving average algorithm), an exponential smoothing forecasting algorithm (e.g., a simple exponential smoothing algorithm, a double exponential smoothing algorithm, a three exponential smoothing algorithm, a Winters exponential smoothing algorithm), a trend extrapolation forecasting algorithm, a regression forecasting algorithm, a grey forecasting algorithm, an autoregressive integrated moving average (ARIMA) algorithm, or the like, or any combination thereof. In some embodiments, Degree 0 was mostly frequently used during a certain period (e.g., past 30 days from the current time) among the one or more prior gantry angle values. In some embodiments, Degree 0 may be equal to an average value of the one or more prior gantry angle values.

In some embodiments, initializing the gantry angle of the medical device using Degree 0 may reduce the time of adjusting the X-ray source to a gantry angle for a scan to be performed on the target object. Description regarding the determination of a gantry angle value of Degree 0 may be found elsewhere in the present disclosure. See, e.g., FIG. 7, and the description thereof.

In some embodiments, 610 may be omitted. The angle determination module 410 (e.g., the angle initialization unit 414) may determine Degree 0 based on an input of a user (e.g., a doctor, an engineer). For example, during a healthy examination of a plurality of people from a company, because scans performed on the plurality of people are same, the user of the medical device 110 may set Degree 0 manually and input Degree 0 to the processing device 140.

In 630, the angle determination module 410 (e.g., the adjustment initialization unit 416) may acquire a pre-set gantry angle Degree 1. In some embodiments, the pre-set gantry angle may be used to a scan to be performed on the target object. The angle determination module 410 may acquire the pre-set gantry angle based on a scan protocol.

In 640, the angle determination module 410 (e.g., the adjustment initialization unit 416) may determine whether Degree 0 is equal to Degree 1. The process 600 may proceed to 650 to adjust the gantry angle from Degree 0 to Degree 1 in response to a determination that Degree 0 is not equal to Degree 1. The process 600 may proceed to 660 to keep the gantry angle at Degree 0 in response to a determination that Degree 0 is equal to Degree 1.

In some embodiments, before 610, the angle determination module 410 may determine whether a prior scan performed closest to a current time has been completed by the medical device 110. In response to a determination that the prior scan performed closest to the current time has been completed by the medical device 110, the angle determination module 410 may perform 610-660.

Figure 7:
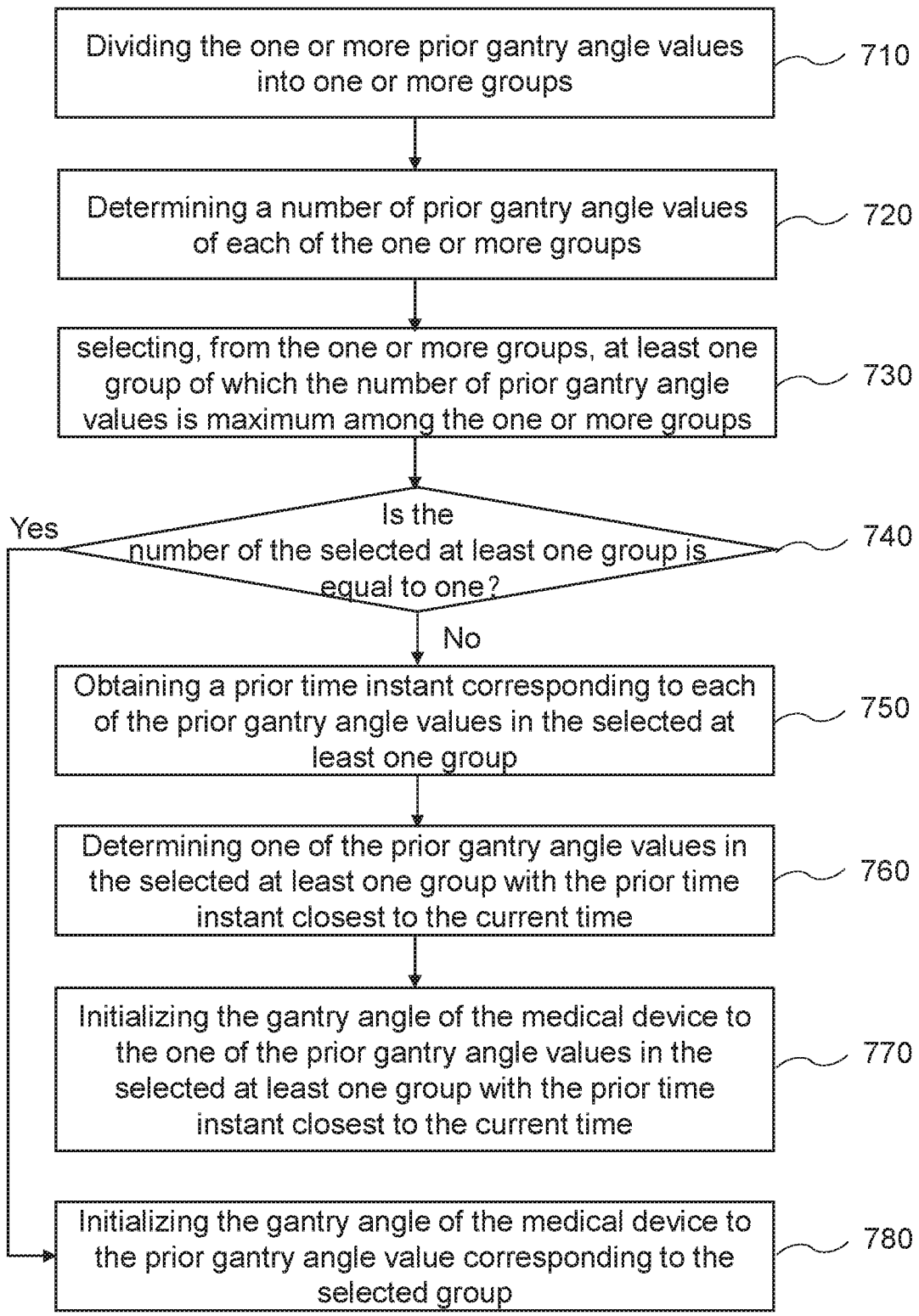
FIG. 7 is a flowchart illustrating an exemplary process for determining an initialized gantry angle of a medical device according to some embodiments of the present disclosure.

FIG. 7 is a flowchart illustrating an exemplary process for determining a gantry angle value based on one or more prior gantry angle values according to some embodiments of the present disclosure. The process 700 may be implemented in the adjustment system 100 illustrated in FIG. 1. For example, the process 700 may be stored in the storage device 150 and/or the storage 220 in the form of instructions (e.g., an application), and invoked and/or executed by the processing device 140 (e.g., the processor 210 illustrated in FIG. 2, or one or more modules in the processing device 140 illustrated in FIG. 4). The operations of the illustrated process presented below are intended to be illustrative. In some embodiments, the process 700 may be accomplished with one or more additional operations not described, and/or without one or more of the operations discussed. Additionally, the order in which the operations of the process 700 as illustrated in FIG. 7 and described below is not intended to be limiting. In some embodiments, step 620 illustrated in FIG. 6 may be performed according to the process 700.

In 710, the angle determination module 410 (e.g., the angle initialization unit 414) may divide the one or more prior gantry angle values into one or more groups. In some embodiments, the angle determination module 410 may put equal prior gantry angle values into a same group.

In 720, the angle determination module 410 (e.g., the angle initialization unit 414) may determine a number of prior gantry angle values of each of the one or more groups.

In 730, the angle determination module 410 (e.g., the angle initialization unit 414) may select, from the one or more groups, at least one group of which the number of prior gantry angle values is maximum among the one or more groups.

In 740, the angle determination module 410 (e.g., the angle initialization unit 414) may determine whether the number of the selected at least one group is equal to one. The process 700 may proceed to 780 to initialize the gantry angle of the medical device 110 to the prior gantry angle value corresponding to the selected group in response to a determination that the number of the selected at least one group is equal to one. The process 700 may proceed to 750 in response to a determination that the number of the selected at least one group is more than one.

In 750, the angle determination module 410 (e.g., the angle initialization unit 414) may obtain a prior time instant corresponding to each of the prior gantry angle values in the selected at least one group. The prior time instant may be the time when the prior gantry angle value was used in a previous scan. The angle determination module 410 may obtain the prior time instant from a storage medium (e.g., the storage device 150, the storage 220).

In 760, the angle determination module 410 (e.g., the angle initialization unit 414) may determine one of the prior gantry angle values in the selected at least one group with the prior time instant closest to the current time.

In 770, the angle determination module 410 (e.g., the angle initialization unit 414) may initialize the gantry angle of the medical device (e.g., the medical device 110) to the one of the prior gantry angle values in the selected at least one group with the prior time instant closest to the current time. In some embodiments, the angle determination module 410 may determine the one of the prior gantry angle values in the selected at least one group with the prior time instant closest to the current time as Degree 0.

In some embodiments, in response to the determination that the number of the selected at least one group is more than one, the angle determination module 410 (e.g., the angle initialization unit 414) may determine an average value of the prior gantry angle values corresponding to the selected at least one group. The angle determination module 410 (e.g., the angle initialization unit 414) may initialize the gantry angle of the medical device 110 to the average value of the prior gantry angle values corresponding to the selected at least one group.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

In some embodiments, the processing device 140 may configure the medical device 110 before performing a medical procedure on a target object based on the process 500, the process 600, and the process 700. For example, when the process 500 proceeds to 570 (e.g., the mode adjustment module 420 determines that the medical device 110 has completed the current scan performed on the target object and determines that the medical device 110 does not satisfy a condition to get into the standby mode), the angle determination module 410 may perform 610 and 620 in the process 600 and/or the process 700 to initial the gantry angle of the medical device 110. Another example may be described in FIG. 8.

Figure 8:
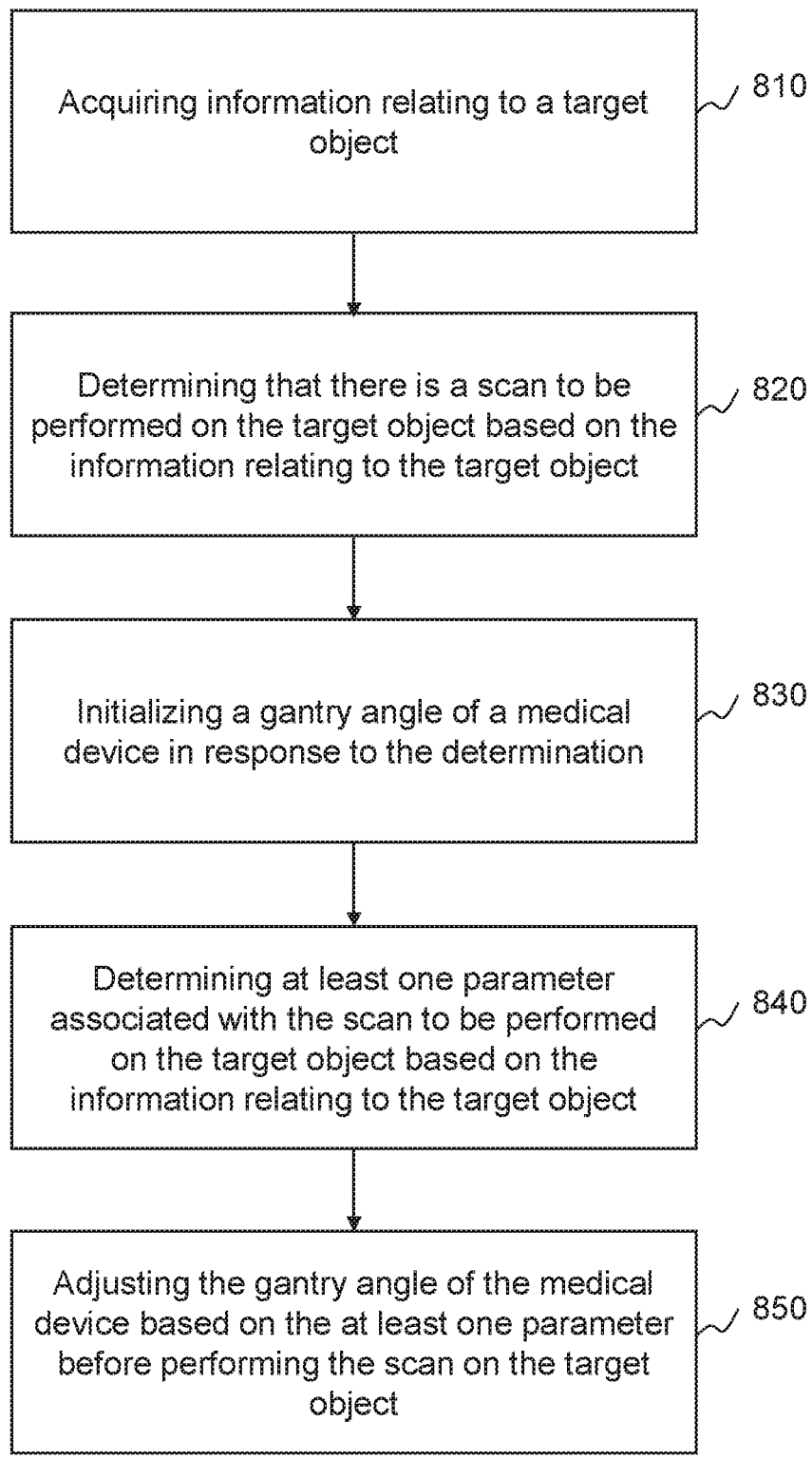
FIG. 8 is a flowchart illustrating an exemplary process for adjusting a gantry angle of a medical device according to some embodiments of the present disclosure.

FIG. 8 is a flowchart illustrating an exemplary process for adjusting a gantry angle of a medical device according to some embodiments of the present disclosure. The process 800 may be implemented in the adjustment system 100 as illustrated in FIG. 1. For example, the process 800 may be stored in the storage device 150 and/or the storage 220 in the form of instructions (e.g., an application), and invoked and/or executed by the processing device 140 (e.g., the processor 210 illustrated in FIG. 2, or one or more modules in the processing device 140 illustrated in FIG. 4). The operations of the illustrated process presented below are intended to be illustrative. In some embodiments, the process 800 may be accomplished with one or more additional operations not described, and/or without one or more of the operations discussed. Additionally, the order in which the operations of the process 800 as illustrated in FIG. 8 and described below is not intended to be limiting. In some embodiments, the process 500 in FIG. 5, the process 600 in FIG. 6, or the process 700 in FIG. 7 may be applied to the process 800.

In 810, the mode adjustment module 420 (e.g., the information acquisition unit 422) may acquire information relating to a target object. In some embodiments, before 810, the mode adjustment module 420 may determine that the medical device 110 is in a standby mode. Description regarding the acquisition of the information relating to the target object may be found elsewhere in the present disclosure. See, e.g., 510 in FIG. 5, and the description thereof.

In 820, the mode adjustment module 420 (e.g., the analysis unit 424) may determine that there is a medical procedure (e.g., a scan) to be performed on the target object based on the information relating to the target object. Description regarding the acquisition of the information relating to the target object may be found elsewhere in the present disclosure. See, e.g., 520 in FIG. 5, and the description thereof.

In 830, the angle determination module 410 (e.g., the angle initialization unit 414) may initialize a gantry angle of a medical device (e.g., the medical device 110) in response to the determination. Description regarding the initialization of the gantry angle may be found elsewhere in the present disclosure. See, e.g., 610 and 620 in FIG. 6, and the process 700 in FIG. 7, and the description thereof.

In 840, the mode adjustment module 420 (e.g., the analysis unit 422) may determine at least one parameter associated with the medical procedure to be performed on the target object based on the information relating to the target object. In some embodiments, the medical procedure may include a scan performed on the target object. The at least one parameter may include a scan protocol. Description regarding the determination of the at least one parameter may be found elsewhere in the present disclosure. See, e.g., FIG. 5, and the description thereof.

In 850, the angle determination module 410 (e.g., the adjustment initialization unit 416) may adjust the gantry angle of the medical device based on the at least one parameter before performing the medical procedure on the target object. Description regarding the adjustment of the gantry angle may be found elsewhere in the present disclosure. See, e.g., 630-660 in FIG. 6, and the description thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, 830 may be performed before or after 840. As another example, 830 and 840 may be performed simultaneously.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the users computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

We claim:

1. A system for configuring a medical device for a medical procedure comprising:
   one or more storage media comprising a set of instructions; and
   one or more processors configured to communicate with the one or more storage media, wherein when executing the set of instructions, the one or more processors are configured to cause the system to:
   before performing a new scan on a target object, initialize a gantry angle of the medical device of the new scan based on one or more prior gantry angle values selected by the system; comprising:
   acquiring the one or more prior gantry angle values of the medical device;
   dividing the one or more prior gantry angle values into one or more groups based on size of the one or more prior gantry angle values;
   for each of the one or more groups, determining a number of prior gantry angle values of the group;
   selecting, from the one or more groups, at least one group of which the number of prior gantry angle values is maximum among the one or more groups; and
   determining that a number of the selected at least one group is more than one and then either
   obtaining a prior time instant corresponding to each of the prior gantry angle values in the selected at least one group in response to the determination, determining one of the prior pantry angle values in the selected at least one group with the prior time instant closest to a current time, and initializing the gantry angle of the medical device to the one of the prior gantry angle values in the selected at least one group with the prior time instant closest to the current time; or
   determining an average value of the prior gantry angle values corresponding to the selected at least one group in response to the determination; and initializing the gantry angle of the medical device to the average value of the prior gantry angle values corresponding to the selected at least one group.

2. The system of claim 1, wherein
   the one or more prior gantry angle values corresponds to one or more prior scans performed prior to the current time.

3. The system of claim 1, the one or more processors are further configured to cause the system to:

before initializing the gantry angle of the medical device of the new scan, determine that a prior scan performed closest to the current time has been completed by the medical device.

4. The system of claim 1, the one or more processors are further configured to cause the system to:
obtain a pre-set gantry angle associated with the new scan;
determine whether the initialized gantry angle is inconsistent with the pre-set gantry angle; and
adjust the initialized gantry angle of the medical device to the pre-set gantry angle in response to a determination that the initialized gantry angle is inconsistent with the pre-set gantry angle.

5. The system of claim 4, wherein the one or more processors are further configured to cause the system to obtain the pre-set gantry angle based on a scan protocol.

6. The system of claim 1, wherein the one or more processors are further configured to cause the system to initialize the gantry angle based on an input of a user.

7. A method for configuring a medical device for a medical procedure implemented on a computing device having one or more processors and one or more storage media, the method comprising:
before performing a new scan on a target object, initializing a gantry angle of the medical device of the new scan based on one or more prior gantry angle values selected by the computing device; comprising:
acquiring the one or more prior gantry angle values of the medical device:
dividing the one or more prior gantry angle values into one or more groups based on size of the one or more prior gantry angle values;
for each of the one or more groups, determining a number of prior gantry angle values of the group;
selecting, from the one or more groups, at least one group of which the number of prior gantry angle values is maximum among the one or more groups; and
determining that a number of the selected at least one group is more than one and then either
obtaining a prior time instant corresponding to each of the prior gantry angle values in the selected at least one group in response to the determination, determining one of the prior gantry angle values in the selected at least one group with the prior time instant closest to a current time, and initializing the gantry angle of the medical device to the one of the prior gantry angle values in the selected at least one group with the prior time instant closest to the current time; or
determining an average value of the prior gantry angle values corresponding to the selected at least one group in response to the determination; and initializing the gantry angle of the medical device to the average value of the prior gantry angle values corresponding to the selected at least one group.

8. The method of claim 7, wherein the one or more prior gantry angle values corresponds to one or more prior scans performed prior to the current time.

9. The method of claim 7, the method further comprising: before initializing the gantry angle of the medical device of the new scan, determine that a prior scan performed closest to the current time has been completed by the medical device.

10. The method of claim 7, the method further comprising:
obtaining a pre-set gantry angle associated with the new scan;
determining whether the initialized gantry angle is inconsistent with the pre-set gantry angle; and
adjusting the initialized gantry angle of the medical device to the pre-set gantry angle in response to a determination that the initialized gantry angle is inconsistent with the pre-set gantry angle.

11. The method of claim 10, wherein the method further comprises obtaining the pre-set gantry angle based on a scan protocol.

12. The method of claim 7, wherein the method further comprises initializing the gantry angle based on an input of a user.

13. A non-transitory computer readable medium of a medical device, the medium comprising executable instructions that, when executed by at least one processor of the medical device, cause the at least one processor to effectuate a method comprising:
before performing a new scan on a target object, initializing a gantry angle of the medical device of the new scan based on one or more prior gantry angle values selected by the at least one processor; comprising:
acquiring the one or more prior gantry angle values of the medical device;
dividing the one or more prior gantry angle values into one or more groups based on size of the one or more prior gantry angle values;
for each of the one or more groups, determining a number of prior gantry angle values of the group;
selecting, from the one or more groups, at least one group of which the number of prior gantry angle values is maximum among the one or more groups; and
determining that a number of the selected at least one group is more than one and then either
obtaining a prior time instant corresponding to each of the prior gantry angle values in the selected at least one group in response to the determination, determining one of the prior gantry angle values in the selected at least one group with the prior time instant closest to a current time, and initializing the gantry angle of the medical device to the one of the prior gantry angle values in the selected at least one group with the prior time instant closest to the current time; or
determining an average value of the prior gantry angle values corresponding to the selected at least one group in response to the determination; and initializing the gantry angle of the medical device to the average value of the prior gantry angle values corresponding to the selected at least one group.

14. The non-transitory computer readable medium of claim 13, wherein the one or more prior gantry angle values corresponds to one or more prior scans performed prior to the current time.

15. The non-transitory computer readable medium of claim 13, the method further comprising: before initializing the gantry angle of the medical device of the new scan, determine that a prior scan performed closest to the current time has been completed by the medical device.

16. The non-transitory computer readable medium of claim 13, the method further comprising:
obtaining a pre-set gantry angle associated with the new scan;
determining whether the initialized gantry angle is inconsistent with the pre-set gantry angle; and
adjusting the initialized gantry angle of the medical device to the pre-set gantry angle in response to a determination that the initialized gantry angle is inconsistent with the pre-set gantry angle.

17. The medium of claim 16, wherein the method further comprises obtaining the pre-set gantry angle based on a scan protocol.

18. The medium of claim 13, wherein the method further comprises initializing the gantry angle based on an input of a user.

* * * * *